(12) United States Patent
Dishaw et al.

(10) Patent No.: US 7,001,065 B2
(45) Date of Patent: Feb. 21, 2006

(54) OILFIELD THREAD MAKEUP AND BREAKOUT VERIFICATION SYSTEM AND METHOD

(75) Inventors: Raymond Dishaw, Anna, TX (US); Terry Eckel, Odessa, TX (US)

(73) Assignee: Ray Dishaw, Anna, TX (US)

( * ) Notice: Subject to any disclaimer, the term of this patent is extended or adjusted under 35 U.S.C. 154(b) by 71 days.

(21) Appl. No.: 10/836,785

(22) Filed: Apr. 30, 2004

(65) Prior Publication Data

US 2004/0223533 A1  Nov. 11, 2004

Related U.S. Application Data

(60) Provisional application No. 60/467,893, filed on May 5, 2003.

(51) Int. Cl.
  *G01N 25/72*  (2006.01)
  *G01N 25/00*  (2006.01)
  *G01J 5/00*  (2006.01)

(52) U.S. Cl. .............. 374/4; 374/45; 374/121

(58) Field of Classification Search .............. 374/4, 374/45, 46, 57, 5; 73/761
See application file for complete search history.

(56) References Cited

U.S. PATENT DOCUMENTS

| | | | |
|---|---|---|---|
| 3,871,209 A | * | 3/1975 | Hasha .................. 73/49.1 |
| 4,573,359 A | | 3/1986 | Carstensen |
| 4,791,816 A | | 12/1988 | Grare et al. |
| 4,957,002 A | | 9/1990 | Coyle et al. |
| 5,042,164 A | | 8/1991 | Eppinger |
| 5,461,905 A | * | 10/1995 | Penisson .................. 73/46 |
| 6,351,997 B1 | * | 3/2002 | Loffler .................. 73/761 |
| 6,405,598 B1 | * | 6/2002 | Bareggi .................. 73/761 |

FOREIGN PATENT DOCUMENTS

| DE | 3229206 A1 | * | 2/1984 |
|---|---|---|---|
| JP | 56153228 A | * | 11/1981 |
| JP | 01216237 A | * | 8/1989 |

* cited by examiner

*Primary Examiner*—Gail Verbitsky
*Assistant Examiner*—Mirellys Jagan
(74) *Attorney, Agent, or Firm*—Browning Bushman P.C.

(57) ABSTRACT

The thread engagement verifier system provides for verifying the quality of a threaded connection 12 between upper and lower for tubular member 16, 18. One or more thermal radiation sensors 14 are used in combination with a data acquisition and processing computer 20 and an output device, such as a video display 12.

The thermal radiation is generated by sliding friction between the tubular members, and the sensors 14 sense radiation at a plurality of external locations and output heat intensity signals to the computer 20. Torque may also be sensed via a sensor 32 and input to the computer 20.

13 Claims, 3 Drawing Sheets

OILFIELD THREAD MAKEUP AND BREAKOUT VERIFICATION SYSTEM AND METHOD

This application claims the benefit of provisional application No. 60/467,893, filed May 5, 2003.

FIELD OF THE INVENTION

The present invention relates to equipment and technique for verifying the quality of a threaded connection between tubular members. More particularly, the present invention relates to the use of a thermal sensor spaced from the tubular connection to remotely sense the temperature at each of a plurality of external points on the tubular connection during the make-up operation, and based upon those readings, determine whether the connection has been properly made-up to withstand the rigors of oilfield operations.

BACKGROUND OF THE INVENTION

When making-up or joining a threaded tubular connection, the drilling operator needs to access the quality of the resulting connection during or immediately after make-up to reduce the likelihood of placing an improperly made-up connection in the well. A reliable threaded connection with both sealing and structural integrity is required to practically conduct oilfield operations, and hundreds of ideas have been proposal for safely, efficiently, and reliably verifying the quality of an oilfield tubular connection during make-up.

A primary tool used to determine the quality of an oilfield tubular threaded connection is the torque between the tubular segments measured during the made-up operation. The degree and uniformity of torque generated when making-up a connection is most commonly used to predict the reliability of the connection. Various U.S. patents describe techniques aimed at evaluating the resulting quality of joined components based on torque measurements. Other variables that may be monitored include strain and/or stress at or near the joint.

U.S. Pat. No. 4,957,002 discloses for determining the quality of assembly of tool parts, wherein a first tool part is assembled with a second tool part by rotatably inserting the first tool part into the second tool part to form a joint. The method comprises the steps of (a) measuring at least one of the rates of rotation of the first and second tool parts and the torque imposed on the first and second tool parts to obtain a first set of data; (b) measuring at least two of axial strain, torsional strain, and hoop strain imposed on the joint to obtain a second set of data, and (c) processing the first and second sets of data to determine the quality of assembly of the tool parts.

U.S. Pat. No. 4,791,816 discloses a device for determining when a threaded joint for steel tubes is properly made-up. The device comprises a strain gauge and means for applying said gauge on an external surface near the joint for measuring longitudinal deformations of extension or contraction on the external surface.

A technique for more generally analyzing deformations is disclosed in U.S. Pat. No. 5,042,164. A sensing device and an analysis process are used for determining the shape of the periphery of a cross-section of a body as it deforms over time. The sensing device includes a band attached to the surface of the deformable body along the external peripheral path of the desired geometrical cross-section. The band has sensing devices on it, each of which produces an output proportional to local curvature as the band is deformed. The analysis process integrates the outputs from the sensing devices to calculate the shape of the periphery of a cross-section of the body to which the band is attached.

Another system for determining the quality a tubular connection during makeup of successive sections of pipe is disclosed in U.S. Pat. No. 4,573,359. A deformation resistant member having point contact engagement with a pipe collar includes a sensor wrapped around the collar in the mid-region of its threaded portion. As the pipe is threaded into the collar, bearing forces exerted on the collar are measured by strain gauges in terms of the extension of the sensor. Temperature sensors responsive to the temperatures of the components generate signals for circuits that are used to compensate for thermal effects, so that more accurate readings are hopefully obtained.

Previous techniques attempting to assess the quality of a tubular connection suffer various drawbacks. Some of these drawbacks relate to the requirement that a mechanical device, such as a strain gauge, be placed in direct contact with a portion of the connection at the end of an oilfield joint. This requirement inherently induces such problems, including wear and tear between parts, calibration difficulties, reduced accuracy exacerbated by placing the device in contact with a rough or uneven portion of the connection, temperature-dependent and pressure-dependent influences on the system, and the time and expense of installing, maintaining, and setting up the system.

A better system and method have long been desired for evaluating the quality of an oilfield tubular threaded connection. The disadvantages of the prior art are overcome by the present invention, and an improved system and method are hereinafter disclosed for verifying the quality of a tubular threaded connection during the make-up operation.

SUMMARY OF THE INVENTION

A system for verifying the quality of the threaded connection between oilfield tubulars or rods includes a thermal radiation sensor directed at the threaded connection to sense thermal radiation emitted from a plurality of external locations on the connection during a makeup operation, a data acquisition and processing computer in communication with the thermal radiation sensor, and an output device in communication with the computer for outputting representations of the quality of the threaded connection as a function of heat intensity signals. Thermal radiation results at least in part from heat generated by sliding friction between the tubular members during the makeup operation, and the thermal radiation sensor outputs heat intensity signals corresponding to each of the plurality of locations.

According to a method of the invention, one may verify the quality of the threaded connection between the oilfield threaded members by spacing a thermal radiation sensor from the threaded connection, threadably rotating at least one of the oilfield threaded members such that sliding friction between the tubular members produces thermal radiation, sensing the thermal radiation at a plurality of external locations on the threaded connection using the thermal radiation sensor, and outputting heat intensity signals corresponding to the sensed thermal radiation at each of the plurality locations.

It is a feature of the invention that a torque sensor may be used for measuring torque on the threaded connection, with the torque sensor outputting torque level signals. The computer may receive a torque level signal and process both heat intensity signals and torque level signals to produce representations of the quality of the threaded connection.

It is a further feature of the invention that the computer may compare the heat intensity signals at one or more locations with heat intensity signals at other of the locations. The computer may also compare the heat intensity signals with one or more predetermined reference heat intensity signals. It is another feature of the invention that the output device may output an estimated torque signal as a function of the heat intensity signals, and may display colors as a function of the heat intensity signals at each of the plurality of locations. A thermal radiation sensor may comprise an infrared camera or radiometric camera. The representations are preferably output while rotatably making up the connection at the well site. One or more thermal radiation sensors may output an intensity signal at each of the plurality of axially spaced locations on the box of the threaded connection.

It is a feature of the present invention that the thermal radiation sensor detects temperature changes when the external surface of the connection are greater than above 0.01° C., preferably above 0.02° C., and in many application above 0.05° C. or greater. The wireless telemetry system may be used for transferring data between the computer and the output device.

According to a method of the invention, it is a feature to create a data set consisting of a plurality of different reference heat intensities and corresponding reference magnitudes of torque, selecting a reference heat intensity from the data set closest to the value of the sensed heat intensity, and outputting the reference magnitude of torque correspondence for the selected reference heat intensity as an estimated actual torque. As a further feature of the invention, one may create a data set consisting of the plurality of different reference heat intensities and corresponding reference magnitudes of torque, and interpolate or extrapolate an estimated actual torque at the sensed heat intensity with respect to the data set.

These and further features and advantages of the present invention will become apparent from the following detailed description, wherein reference is made to the figures in the accompanying drawings.

DETAILED DESCRIPTION OF PREFERRED EMBODIMENTS

Figure 1:
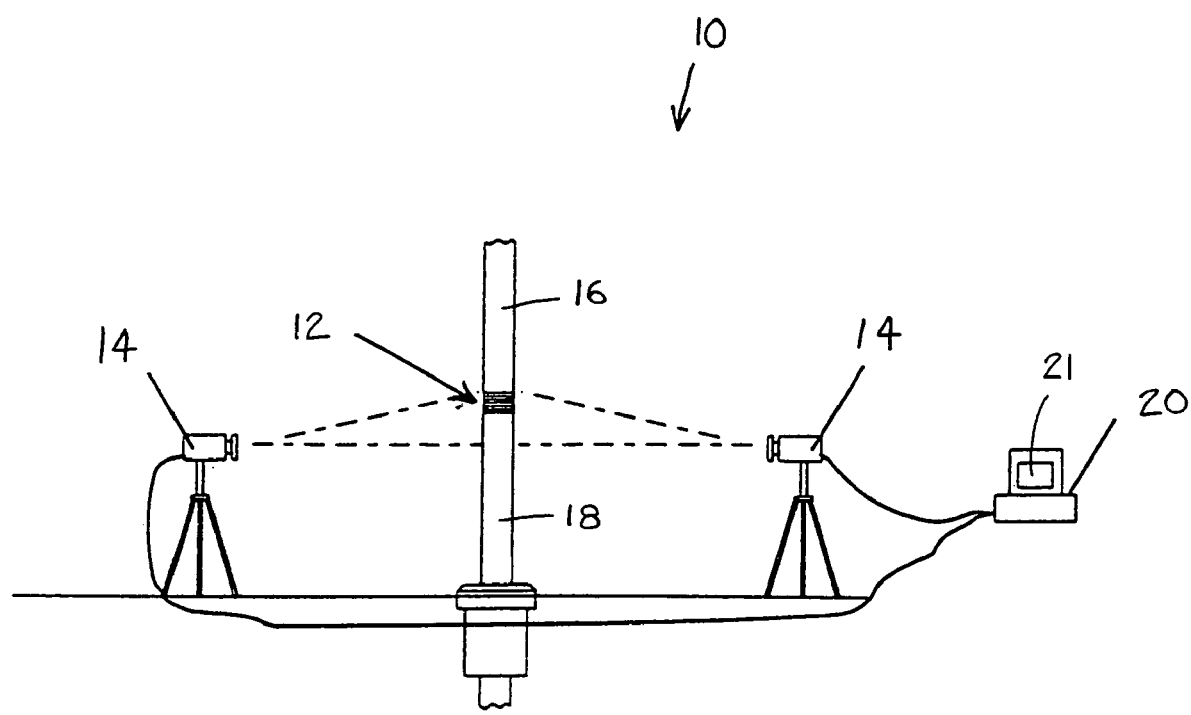
FIG. 1 illustrates the primary components of a system according to the present invention for verifying the quality or uniform make-up of the threaded connection between oilfield tubulars at a rig site.

FIG. 1 illustrates one embodiment of a thread engagement verification system (TEVS) 10 for verifying the quality of a threaded connection 12 between upper and lower oilfield tubular members 16, 18. One or more thermal radiation sensors 14 may be directed at the external surfaces of the threaded connection 12, including particularly two or more axially spaced the external surfaces on the connection. A data acquisition and processing computer 20 is in communication with the sensors 14. An output device, such as a video display 21 is in communication with the computer 20.

In a preferred embodiment, the system of the present invention produces an output which may be viewed by a drilling operator or his representative in substantially real time, i.e., the drilling operator is able to view an output while the connection is made-up, and is practically able to determine, during or at the conclusion of the make-up operation, that the connection has been or has not been properly made-up. The system of the present invention thus has significant advantages over systems which require additional time to place sensors on the oilfield tubular joints and/or connections or systems which inherently require post make-up analysis, wasting valuable rig time to determine if the connection has been properly made-up. Moreover, the system of the present invention may often be used to promptly identify problems associated with the beginning of an improperly made-up or damaged threaded connection, in which case the drilling operator may stop the make-up connection, backout the threads a few turns, inspect the threads and seals, then replace the damaged connection or restart the make-up operation, thereby possibly avoiding the cost and expense of replacing an improperly made-up connection.

Thermal radiation is generated by threadably engaging the tubular members 16, 18, such as may be induced by sliding friction between the tubular members 16, 18 during make-up or break out. The sensors 14 sense thermal radiation (temperature) of plurality of external locations on the threaded connection 12 and output heat intensity signals. The computer 20 receives and processes the heat intensity signals, and outputs representations of the quality of the threaded connection as a function of the outputted heat intensity signals. The representations may be displayed on the output screen 21.

The thermal imaging sensors 14 may include one or more infrared cameras. Alternatively, the sensors 14 may include one or more radiometric cameras. An infrared camera may sense invisible radiation wave lengths, such as from about 750 nanometers, just longer than red in the visible spectrum, to 1 millimeter, on the border of the microwave region. A radiometric camera may similarly sense radiant energy such as electromagnetic radiation. The cameras may or may not be mounted on a tripod.

At least some of the thermal radiation sensed is induced by sliding friction between the threaded members 16, 18 during make-up or break out. The advantage of producing thermal radiation in this manner is that the heat intensity will vary between locations on the threaded connection 12. For example, tight spots between threads of the tubular 16, 18, or nonuniformities along the threads, may increase or decrease friction at different positions, thereby affecting the amount heat generated and thus the thermal radiation produced. Differences in thermal radiation may be sensed between various positions to verify the quality of the threaded connection 12.

In addition to inducing thermal radiation with friction; some radiation may also be produced naturally, such as by absorption of light rays from the sun, but these sources of radiation tend to uniformly affect the connection and thus do not produce significant changes in temperature between spaced locations.

The output device 21 may preferably be a video display 21, and representations of quality outputted by the computer 20 may be a color representation corresponding to the heat intensity signals. For example, the color representation may be a thermal "image" of the male and female ends at the threaded connection, with colors at each location corresponding to the heat intensity. Thermal image may reveal imperfections or dislocations as hot or cold spots, with a correspondingly different color at one location contrasting with the displayed color at other locations. In other embodiments, the output device 21 may represent a chart or graph as a function of the heat intensity at different locations. The output device 21 may generate a hard copy printout, such a chart or graph, or may transmit the data in real time to an office hundreds or thousands of miles from the rig. The output device 21 may also sound an alarm to notify rig personnel that an abnormality has occurred.

A torque sensor preferably is provided for measuring actual torque on the threaded connection. The torque sensor and the thermal radiation sensor may thus provide complimentary analyses and verifications of the threaded connection. For example, if the torque sensor indicates an unusually high level of torque, the thermal radiation sensor may display a corresponding defect or other anomaly. Alternatively, if the torque sensor indicates a "normal" level of torque, the thermal radiation sensor may display otherwise hidden defects or problem areas in the threaded connection 12.

Figure 3:
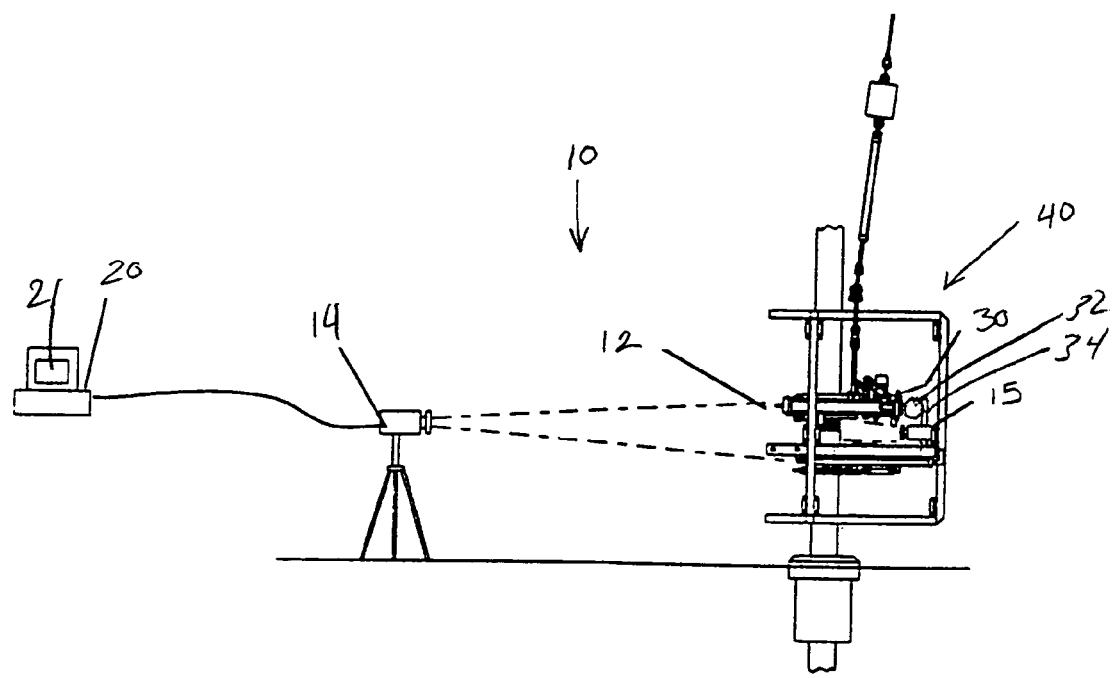
FIG. 3 illustrates yet another embodiment of a tubular make-up verification system.

Torque may be conventionally measured by a torque sensor connected to the frame of the power tong, and in a preferred application torque is measured by sensor 32 sensing the force on a stinger 34 acting between the power tong and a backup tong, as shown in FIG. 3. Torque signals may be transmitted to the computer 20 via wireline 42. The computer may thus recognize input from both the camera and a torque sensor 32, and used the combination of data to disclaim the quality of the threaded connection.

The computer 20 may compare the heat intensity signals at one or more locations in real time. The quality of the threaded connection 12 may then be verified with the comparison. In one embodiment, a predetermined heat intensity signal is stored in a computer for each specific type of thread connection, along with a variable band for the range of temperatures above and below a signature line, which are deemed acceptable. During the make-up operation, the computer receives the heat intensity signals as the make-up operation progresses, the computer may output a signature in a substantially real time for the connection being made-up time. The computer may thus determine that one connection has been properly made-up since the heat intensity signature for that connection during the entire make-up operation was within the acceptable band from the predetermined signature line, and alternatively may determine that, at one or more locations, the signal being generated for a specific connection passes outside of the acceptable band width, in which case, the computer may determine that the connections may have been improperly made-up. More specific programs may cause the computer to tentatively reject a connection only if the band width is exceeded by a predetermined amount and/or a predetermined time. In many applications, the drilling operator, once alerted to the possibility of a poorly made-up connection, may review the data on a screen, then determine whether the connection should be placed in the well or whether the connection should be broken out or replaced and again made-up. Even when the drilling operator determines to place the threaded connection in the well, if an output signal was briefly outside the band width, valuable information has been obtained, since specific data for that connection may be easily transmitted and stored in the same or another computer or database, then the made-up connection physically evaluated days, weeks, or months later when the connection is returned to the surface and is broken out. A comparison of the heat intensity signature for a specific connection and the physical review and inspection of that connection when returned to the surface may thus enable an operator to better define the predetermined heat intensity signature for that specific type of connection and/or revise the band width from that signature at various stages of the make-up operation.

The computer 20 may thus compare the heat intensity signals with one or more predetermined reference heat intensities. The computer may further select a reference magnitude of torque corresponding with the one or more reference heat intensities. The selected reference magnitude of torque may be displayed or represented on the output device 21 to be an estimated actual torque. For example, if two pairs of reference heat intensity vs. reference magnitude of torque are (140° F., 4000 ft-lbs torque on tubular) and (160° F., 7000 ft-lbs torque on tubular), and a sensed heat intensity is 19, the computer may select the pair (140°, 4000 ft-lbs) and display this information as the estimated actual torque. The computer may likewise interpolate or extrapolate an estimated actual torque with respect to the reference heat intensities and reference magnitudes of torque. For example, using the above two reference pairs, if a sensed heat intensity is 150° F. (halfway between 140° F. and 160° F.), an estimated actual torque may be interpolated as 5500 ft-lbs (half way between 4000 ft-lbs and 7000 ft-lbs). Likewise, if a sensed heat intensity is 170°, the computer may extrapolate an estimated actual torque to be 8000 ft-lbs based on the reference pairs.

In order to perform its function of verifying the quality of an oilfield tubular threaded connection during the make-up operation, the thermal radiation sensor must be extremely sensitive. Drilling operators have long known that heat is generated during the make-up operation, but it is surprising that a remote radiation sensor could be used to detect very small changes in temperature between different locations on the connection and thereby effectively determine whether the connection is properly made-up. One preferred type of radiation sensor according to the present invention is a Merlin Model NIR infrared camera which is able to accurately determine temperature changes at different external locations on a connection of about 0.018° C. Another suitable sensor is the thermal camera manufactured by Indigo under Model TVS-700, which has a tolerance of about 0.08° C. In a preferred embodiment, the temperature sensor of the present invention is able to detect temperature variations at different locations on the connection which are about 0.05° C. or greater.

Cameras the type discussed above are generally not desired at a rig site, where operating and environmental condition vary widely. Nevertheless, the system of the present invention could be widely accepted as a useful tool to determine if an oilfield threaded connection has been properly made up. The inherent consequences of not determining an improperly made-up connection may be hundreds of thousands of dollars to the loss of the oil well, which could cost millions of dollars. Also, none of the components used in the system, including the thermal radiation sensor or camera, the computer, or the output device need to contact the threaded connection or the oilfield tubulars, or even need be spaced closely adjacent to the connection to perform the desired function. To the contrary, each of the cameras, the computer, and output device may be spaced a meter or more from the threaded connection, depending on the desires of the drilling operator, the rig layout, environmental conditions and other factors. Moreover, the components of the system do not need be moved closer to the connection during the make-up operation then moved laterally away from the connection to allow sufficient rig floor space for conducting other operations which occurs between successive make-up operations. In a suitable application, the camera may be 25 or 30 feet from the threaded connection. The value of the output data should overcome the comprehensions of oilfield personnel to using sophisticated equipment.

Radiation sensors other than cameras may be used to achieve the objectives of the invention, although a camera is the preferable form of sensor because it allows the viewer to view, in real time, an output which is graphically very similar to the events occurring. In other words, the camera output may be programmed to show different shades of red for the intensity of a hot zone, various shades of orange for intermediate temperature zones, shades of green for still cooler temperature zones, and finally shades of blue for the lowest temperature signals being monitor. Blue represents the coolest temperatures while red is the hottest temperatures. Also, it should be noted that the system of the present invention is able to utilize various electronic data transmission systems, and particularly wireless data transmission systems, to transmit data from the sensor to the computer, and then from the computer to a remote location, or alternatively from the sensor through a wireless transmission system to a remote computer and a remote output device, so that make-up of the threaded connection at an offshore well site may be transmitted in real time to a land based operation hundreds or thousands of miles from the well.

In a preferred embodiment of the invention, one or more radiation sensors are used to detect the temperature at each of the plurality of axially spaced locations on the box of the threaded connection. In other words, a temperature sensor may be directed to the pin connection, but since the pin is mostly in the box or coupling during the make-up operation, it is preferable that at least two of the thermal radiation sensors be directed at axially spaced locations on the external surface of the box or coupling. Depending on the connection, the sensors may be directed to three particular connections, for example, (1) an area adjacent a shoulder on the connection, (2) another area adjacent one of the seals of the connection, and (3) area most representative of the temperature of central body of the box. One camera can view a 180° side of the connection, and a second camera used to view the opposing 180° side of the connection.

Figure 2:
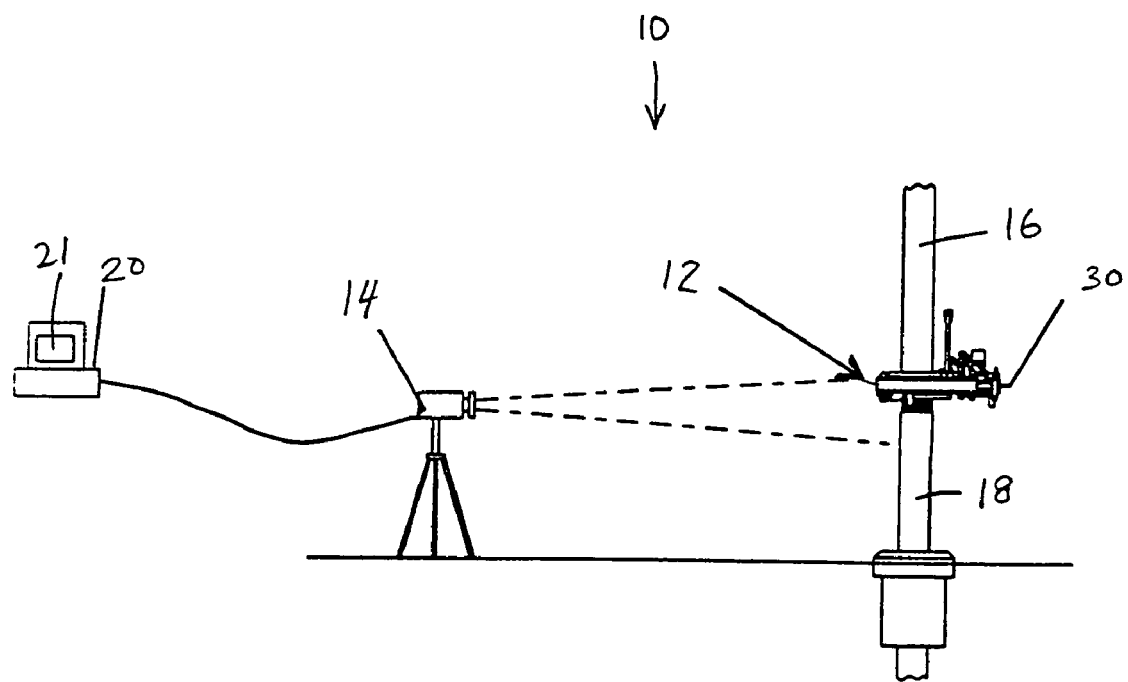
FIG. 2 illustrates an alternate embodiment of a system according to the present invention.

FIG. 2 illustrates another embodiment of the ATVS 10 used in conjunction with a power tong 30. The power tong 30 is used to rotatably engage the upper tubular 16 and the fixed lower tubular 18, i.e. to make-up or break out the connection 12. Friction generated between the upper and lower tubular threads may generate thermal radiation to be sensed and processed by an automated thread verification system (ATVS) 10.

FIG. 3 illustrates another embodiment of the ATVS 10 in which the connection is made-up using an automated tong positioning system (ATPS) 40. The tong 30 on the ATVS 40 is used to make-up or break out the connection 12. Friction generated between the upper and lower tubular threads 16, 18 may generate thermal radiation to be sensed and processed by the ATVS 10. The sensor 14 radially spaced from the connection 12 is complimented by another sensor 15 positioned on or near the ATVS 10. The sensors 14, 15 may provide thermal imaging data to the computer 20.

The system as disclosed herein is particularly suitable for verifying the quality of an oilfield threaded connection. In another oilfield application, the system may be used to determine the quality of a threaded connection between sucker rods in a string. Also, the system and method may be used for determining the quality of threaded connections, and/or the heating the components of the threaded connection, wherein the connection is either between two oilfield tubular products, such as casing, drill pipe, or sucker rods, or between more standard threaded connections, such as on rods, bolts, and riser tensioner connections, including a plurality of the circumferentially spaced bolts each highly torqued to maintain a high pressure seal between two flanges of a high pressure line.

The present invention may use infra-red imaging, qualitative nonradiometric, thermo measurement thermography, or a quantitative radiometric measurement camera system for the thermal radiation sensor for verifying tubular matching threads being connected (male to female) on all threaded materials, whether metal, metallic, non-metallic, ferris or non ferris, plastic, or any threaded connections while being made up, screwed together, fitted, connected or assembled together.

The qualitative, nonradiometric camera is not calibrated to give an absolute calibrated temperature measurement value, such as when the thread is made up on a quantatative or radiometric system which will produce an absolute temperature, such as a 140°. A qualitative, nonradiometric camera shows the imaging of a temperature profile, but does not produce temperature value readouts from the image shown on the screen. A quantitative measurement system also allows for the production of charts and graphs based on absolute temperature measurements.

Using a camera for sensing the drill pipe connection, the operator can see on a monitor and the computer can determine the proper heat signature on the drill pipe shoulder to determine a good shoulder seal. The heat signature or lack of a good heat signature will determine if the pin is too long for the connection and/or the shoulder is not making a good seal with limited or no torque being applied to the shoulder of the drill pipe connection.

One use will be to verify matching threads on all oilfield tubular threaded connections while being connected. This method will utilize the system to verify the integrity of the threaded connection. This system can detect and display heat being generated by the friction of the matching threads, corrupted and/or cross-threaded, as well as determine the heat variation in areas where threads are not matching or uniform. The software allows one to analyze and produce histograms, graphs, predictions, and hot spots as well as overall area heat variances and thermal analysis.

When there is a uniform connection, a uniform heat signature will be displayed across the female connection, increasing in intensity as the torque increases, indicating a good connection. When any abnormal connection is being made, a heat signature will be displayed in the area of the connection that is having the abnormality, and will be absent in an area where little or no heat is generated.

Torque can be determined by the intensity of the heat signature. This is accomplished by giving the heat signature a torque reference point or points in the computer database software. One can determine the torque being developed by the increasing intensity of the heat signature on the connection. This allows the computer, in real time, to compute and determine the torque on a threaded connection being connected or backed out without physically touching the connection. This information can be stored for future reference for each connection. There will be many uses for this system, including connecting oilfield pipe, drill pipe, casing, tubing, riser tensioners, bucking on collars, and sucker rod connections. This system will also allow one to determine life projections on the connections, joint wear variances, mismatched threads, cross-threads, damaged threads, and torque on the connection.

The equipment of the present invention is ideally suited to the oil industry, which requires equipment to be rugged and withstand both onshore and offshore standards. The equipment may also withstand various industrial application standards, and may be packaged and designed for these types of applications.

While preferred embodiments of the present invention have been illustrated in detail, it is apparent that other modifications and adaptations of the preferred embodiments will occur to those skilled in the art. The embodiments shown and described are thus exemplary, and various other modifications to the preferred embodiments may be made which are within the spirit of the invention. Accordingly, it is to be expressly understood that such modifications and adaptations are within the scope of the present invention, which is defined in the following claims.

What is claimed is:

1. A system for verifying the quality of a threaded connection between oilfield members, comprising:
    a thermal radiation sensor directed at the threaded connection to sense thermal radiation emitted from a plurality of external locations on the threaded connection during a make-up or breakout operation, the thermal radiation resulting at least in part from heat generated by sliding friction between the oilfield members during the makeup operation, the thermal radiation sensor outputting heat intensity signals corresponding to each of the plurality of locations;
    a data acquisition and processing computer in communication with the thermal radiation sensor for receiving and processing the outputted heat intensity signals; and
    an output device in communication with the computer for outputting representations of the quality of the threaded connection as a function of the outputted heat intensity signals.

2. A system as defined in claim 1, further comprising:
    a torque sensor for measuring torque on the threaded connection, the torque sensor outputting torque level signals; and
    the computer receives the torque level signals and processes both heat intensity signals and torque level signals to generate the representations of the quality of the threaded connection.

3. A system as defined in claim 1, wherein the computer compares the heat intensity signals at one or more of the locations with the heat intensity signals at other of the locations.

4. A system as defined in claim 1, wherein the computer compares the heat intensity signals with one or more predetermined reference heat intensity signals.

5. A system as defined in claim 1, wherein the output device outputs an estimated torque signal as a function of the heat intensity signals.

6. A system as defined in claim 1, wherein the output device displays colors as a function of the heat intensity signals at each of the plurality of locations.

7. A system as defined in claim 1, wherein the thermal radiation sensor comprises an infrared camera.

8. A system as defined in claim 1, wherein the thermal radiation sensor comprises a radiometric camera.

9. A system as defined in claim 1, wherein the representations are output while rotatably making-up the threaded connection.

10. A system as defined in claim 1, wherein the oilfield threaded members include an upper tubular and lower threaded connection, and the thermal radiation sensor is positioned at a well site.

11. A system as defined in claim 1, wherein the thermal radiation sensor comprises one or more thermal radiation sensors for outputting heat intensity signals at each of a plurality of axially spaced locations on the box of the threaded connection.

12. A system as defined in claim 1, wherein the thermal radiation sensor detects temperatures changes when the external surface of the connection are greater than about 0.01° C., preferably above 0.02° C. or greater, and many application about 0.05° C. or greater.

13. A system as defined in claim 1, further comprising:
    a wireless telemetry system transferring data between the computer and the output device.

* * * * *